United States Patent [19]

Smith et al.

[11] Patent Number: 5,414,124
[45] Date of Patent: May 9, 1995

[54] METHOD OF PREPARING QUARTERNARY AMMONIUM FORMULATIONS WITH HIGH FLASH POINTS

[75] Inventors: Kim R. Smith; Frederick M. Boyd, both of Huntington; Samih S. Abouhalkah, Fort Wayne, all of Ind.

[73] Assignee: Huntington Laboratories, Inc., Huntington, Ind.

[21] Appl. No.: 5,731

[22] Filed: Jan. 19, 1993

[51] Int. Cl.$^6$ ............................................. C07C 209/12
[52] U.S. Cl. .................................. 564/282; 564/291; 564/296
[58] Field of Search .................. 564/282, 291, 296; 514/642, 643

[56] References Cited

U.S. PATENT DOCUMENTS

| | | | |
|---|---|---|---|
| 3,472,939 | 10/1969 | Petrocci et al. | 424/329 |
| 3,525,793 | 8/1970 | Petrocci et al. | 424/329 |
| 3,836,669 | 9/1974 | Dadekian et al. | 424/329 |
| 4,165,375 | 8/1979 | Berger et al. | 424/263 |
| 4,238,373 | 12/1980 | Hardy et al. | 252/542 |
| 4,320,147 | 3/1982 | Schaeufele | 424/329 |
| 4,444,790 | 4/1984 | Green et al. | 424/324 |
| 4,450,174 | 5/1984 | Green et al. | 424/329 |
| 4,464,398 | 8/1984 | Sheets et al. | 424/329 |

FOREIGN PATENT DOCUMENTS

| | | | |
|---|---|---|---|
| 0056940 | 4/1985 | Japan | 564/296 |
| 0087246 | 5/1985 | Japan | 564/296 |
| 1221224 | 2/1971 | United Kingdom . | |

*Primary Examiner*—Peter O'Sullivan
*Attorney, Agent, or Firm*—Barnes & Thornburg

[57] ABSTRACT

A quaternary ammonium compound solution comprising from about 50% to about 80% of a quaternary ammonium compound and from about 20% to about 50% of a solvent. The solvent being from about 25% to about 100% of alkylene glycol with the remainder being water. The method of making quaternary ammonium compounds comprises reacting methyl chloride and/or benzyl chloride and dialkylmethylamine and/or alkyldimethylamine in an alkylene glycol to completion and diluting the same with sufficient water to a solution in which the alkylene glycol is from about 25% to about 100% of the solvent component of the total solution and the quaternary ammonium compound is from about 50% weight to about 80% weight of the quaternary ammonium compound solution.

23 Claims, No Drawings

METHOD OF PREPARING QUARTERNARY AMMONIUM FORMULATIONS WITH HIGH FLASH POINTS

BACKGROUND OF THE INVENTION

The present invention relates to germicides and those solutions of quaternary ammonium compounds useful as germicides, and more particularly to solutions of quaternary ammonium compounds which have a flash point greater than 200° F.

Quaternary ammonium compounds have long been used as germicides. Solutions of quaternary ammonium compounds are effective cationic germicides typically manufactured as either a 80% active solution or 50% active solution. The solvent portion of the 80% active solutions are typically ethanol and a mixture of ethanol and isopropanol. The solvent portion of the 50% solutions are typically ethanol, isopropanol and water. Typically these solutions of quaternary ammonium compounds have a flash point from about 100° to about 125° and in all cases less than 200° F.

Recently, (effective on Jan. 1, 1993) the Environmental Protection Agency of the United States Government has declared all such solutions having a flash point below 140° F. as flammable. The designation of these germicide solutions as flammable require every user of such germicides to utilize special precautions as provided in the regulations of the Environmental Protection Agency both as to use and as to disposal. Additionally, the use of such germicidal solutions now deemed flammable by the EPA impose significant liability onto the users of such germicides and are likely to raise premiums on the general liabilty insurance of such users.

Heretofore, it is known that quaternary ammonium compounds are soluble in alcohols and aqueous alcohols. Generally such compounds will crystallize in solvents useful with other materials. Crystallization of such compounds has been observed in water, propylene glycol and other glycols. While quaternary ammonium compounds are known to be soluble in exotic solvents such as dimethylsulfoxide, this solvent would result in a substantial raise in price for quaternary ammonium compound based disinfectants and a frantic search for other disinfectants.

Therefore it is highly desirable to provide an improved quaternary ammonium compound solution which has a flash point above 200° F. and an improved method for making the same.

It is also highly desirable to provide an improved quaternary ammonium compound solution which has a flash point above 200° F. which will not crystallize upon storage at ambient temperatures and an improved method for making the same.

It is also highly desirable to provide an improved quaternary ammonium compound solution which has a relatively long shelf life and an improved method for making the same.

It is also highly desirable to provide an improved quaternary ammonium compound solution which has as its solvent portion no alcohol and an improved method for making the same.

It is also highly desirable to provide an improved quaternary ammonium compound solution which has as its solvent portion a mixture of propylene glycol and water and an improved method for making the same.

It is also highly desirable to provide an improved quaternary ammonium compound solution for use as a cationic disinfectant which has as its solvent portion a mixture of propylene glycol and water which can be supplied as solutions having from about 50% active ingredients to about 80% active ingredients and an improved method for making the same.

Finally, it is highly desirable to provide an improved quaternary ammonium compound solution which can be used as a disinfectant which has all of the above features and an improved method for making the same.

SUMMARY OF THE INVENTION

Therefore it is an object of the invention to provide an improved quaternary ammonium compound solution which has a flash point above 200° F. and an improved method for making the same.

It is also an object of the invention to provide an improved quaternary ammonium compound solution which has a flash point above 200° F. which will not crystallize upon storage at ambient temperatures and an improved method for making the same.

It is also an object of the invention to provide an improved quaternary ammonium compound solution which has a relatively long shelf life and an improved method for making the same.

It is also an object of the invention to provide an improved quaternary ammonium compound solution which has as its solvent portion no alcohol and an improved method for making the same.

It is also an object of the invention to provide an improved quaternary ammonium compound solution which has as its solvent portion a mixture of propylene glycol and water and an improved method for making the same.

It is also an object of the invention to provide an improved quaternary ammonium compound solution for use as a cationic disinfectant which has as its solvent portion a mixture of propylene glycol and water which can be supplied as solutions having from about 50% active ingredients to about 80% active ingredients and an improved method for making the same.

Finally, it is an object of the invention to provide an improved quaternary ammonium compound solution which can be used as a disinfectant which has all of the above features and an improved method for making the same.

In the broader aspects of the invention, there is provided a quaternary ammonium compound solution comprising from about 50% to about 80% of a quaternary ammonium compound and from about 20% to about 50% of a solvent. The solvent being from about 25% to about 100% of alkylene glycol with the remainder being water. The method of making quaternary ammonium compounds comprises reacting methyl chloride and/or benzyl chloride and dialkylmethylamine and/or alkyldimethylamine in an alkylene glycol to completion and diluting the same with sufficient water to a solution in which the alkylene glycol is from about 25% to about 100% of the solvent component of the total solution and the quaternary ammonium compound is from about 50% weight to about 80% weight of the quaternary ammonium compound solution.

DESCRIPTION OF A SPECIFIC EMBODIMENT

There are generally two types of quaternary ammonium compounds. These include:

Benzalkonium Chloride or Bromide

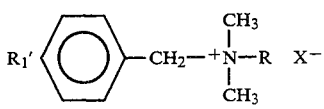

where
R = $C_8$ thru $C_{24}$ alkyl
$R_1'$ = $CH_3$, $C_2H_5$, or H
X = $Cl^-$ or $Br^-$ —and
Dialkyldimethylammonium Chloride or Bromide

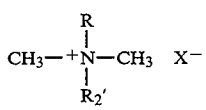

where
R = $C_8$ thru $C_{24}$ alkyl
$R_2'$ = $C_8$ thru $C_{24}$ alkyl
X = $Cl^-$ or $Br^-$ Solutions of these compounds and a solution of a 50%/50% mixture of these compounds are currently being provided by the industry in solutions that are (1) 50% active quaternary ammonium compound and 50% solvent or (2) 80% active quaternary ammonium compound and 20% solvent. The solvent portion of the 50% active quaternary ammonium compound solutions have from about 25% to 50% ethanol and/or isopropanol and the remainder water. The solution component of the 80% active quaternary ammonium compounds are typically either ethanol or isopropanol. Both of the quaternary ammonium compounds crystallize when dissolved in water. All have flash points below 200° F. when dissolved in ethanol, isopropanol, and ethanol and water solvent combinations. See Table I for a summary of undesirable crystallization and flashpoints.

TABLE I

| Solvent | Crystallization | Flash Pt (°F.) |
|---|---|---|
| Benzalkonium Chloride or Bromide | | |
| Water | Yes | doesn't flash |
| Ethanol | No | <200 |
| Isopropanol | No | <200 |
| Propylene glycol | Yes | >200 |
| Ethylene glycol | Yes | 200 |
| Didecyldimethylammonium Chloride or Bromide | | |
| Water | Yes | doesn't flash |
| Ethanol | No | <200 |
| Isopropanol | No | <200 |
| Propylene glycol | No | >200 |
| Ethylene glycol | No | 200 |
| 50/50 mixture of Benzalkonium Chloride or Bromide and Didecyldimethylammonium Chloride or Bromide | | |
| Water | Yes | doesn't flash |
| Ethanol | No | <200 |
| Isopropanol | No | <200 |
| Propylene glycol | Yes | >200 |
| Ethylene glycol | Yes | 200 |

Both ethanol and isopropanol improve the solubility of quaternary ammonium compounds; however no solvent system has heretofore been devised utilizing either ethanol or isopropanol or combinations thereof which result in a flash point above 200° F.

Surprisingly, the same quaternary ammonium compounds which are insoluble in water and ethylene glycol and propylene glycol are soluble in combinations of water and alkylene glycol. For example, benzalkonium chloride is soluble in solvents ranging from about 48% to 84% of alkylene glycol with the remainder water. Similarly, didecyldimethylammonium chloride is soluble in solvents ranging from about 25 to 100% alkylene glycol with the remainder water, and mixtures of both quaternary ammonium compounds are soluble in solvent compositions consistent with the above. Also, surprisingly, mixtures of Benzalkonium Chloride or bromide and didecyldimethyl ammonium chloride or bromide are not soluble in 100% ethanol or propylene glycol or ethylene glycol. See for example Table II for desirable solvent compositions.

TABLE II

| Benzalkonium Chloride or Bromide Solvents | | |
|---|---|---|
| 52% Water 48% Propylene glycol | 80% Solution |
| 16% Water 84% Propylene glycol | 50% Solution |
| 50% Water 50% Propylene glycol | 50% Solution |
| Didecyldimethylammonium Chloride or Bromide | | |
| 52% Water 48% Propylene glycol | 80% Solution |
| 16% Water 84% Propylene glycol | 50% Solution |
| 50% Water 50% Propylene glycol | 50% Solution |
| 50/50 Mixture of Benzalkonium Chloride or Bromide and Didecyldimethylammonium Chloride or Bromide | | |
| 52% Water 48% Propylene glycol | 80% Solution |
| 16% Water 84% Propylene glycol | 50% Solution |
| 50% Water 50% Propylene glycol | 50% Solution |
| 90/10 Mixture of Benzalkonium Chloride or Bromide and Didecyldimethylammonium Chloride or Bromide | | |
| 52% Water 48% Propylene glycol | 80% Solution |
| 16% Water 84% Propylene glycol | 50% Solution |
| 50% Water 50% Propylene glycol | 50% Solution |
| 10/90 Mixture of Benzalkonium Chloride or Bromide and Didecyldimethylammonium Chloride or Bromide | | |
| 52% Water 48% Propylene glycol | 80% Solution |
| 16% Water 84% Propylene glycol | 50% Solution |
| 50% Water 50% Propylene glycol | 50% Solution |

Active cationic germicide solutions including either quaternary ammonium compound and 50% quaternary ammonium compound can be provided with these solvent systems and yet still have a flash point above 200° F., and thus not being classified as flammable by the Environmental Protection Agency and be acceptable for safe use by the airline service industry.

In specific embodiments, the alkylene glycols useful in the invention are represented by:

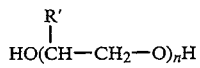

where R' is either a H or a $CH_3$ and n is from about 1 to about 1000.

The following examples will best illustrate the invention.

EXAMPLE 1

A 3 liter flask was charged with 603 g of alkyldimethylamine (40% $C_{12}$, 50% $C_{14}$, 10% $C_{16}$), 327 g of benzyl chloride, and 436g of propylene glycol. The reaction solution was heated to 95°–100° C. and held at that temperature for five hours. A charge of 419 g of water was added to the reaction solution and heating was continued for an additional hour. After the six hours of total reaction time, the react ion mass was cooled to ambient temperature and analyzed. The reaction product was analyzed at 50.16 weight percent quaternary ammonium compound, 0.57% free amine, and 0.06% amine hydrochloride salt. The flash point of the quaternary ammonium compound reaction solution was greater than 200° F.

EXAMPLE 2

A 3 liter flask was charged with 603 g of alkyldimethylamine (40% $C_{12}$, 50% $C_{14}$, 10% $C_{16}$), 327 g of benzyl chloride, and 712g of propylene glycol. The reaction solution was heated to 95°–100° C. and held at that temperature for five hours. A charge of 143 g of water was added to the reaction solution and heating was continued for an additional hour. After the six hours of total reaction time, the reaction mass was cooled to ambient temperature. The flash point of the quaternary ammonium compound reaction solution was greater than 200° F.

EXAMPLE 3

A 3 liter flask was charged with 603 g of alkyldimethylamine (40% $C_{12}$, 50% $C_{14}$, 10% $C_{16}$), 327 g of benzyl chloride, and 410 g of propylene glycol. The reaction solution was heated to 95°–100° C. and held in reaction at that temperature for five hours. A charge of 445 g of water was added to the reaction solution and heating was continued for an additional hour. After the six hours of total reaction time, the reaction mass was cooled to ambient temperature. The flash point of the quaternary ammonium compound reaction solution was greater than 200° F.

EXAMPLE 4

A 2 liter autoclave was charged with 400g of didecylmethylamine 72 g of methyl chloride, and 112 g of propylene glycol. The reaction solution was heated to 95°–100° C. and held in reaction at that temperature for four hours. After the five hours of total reaction time, the reaction mass was cooled to ambient temperature. The flash point of the quaternary ammonium compound reaction solution was greater than 200° F.

EXAMPLE 5

A 2 liter autoclave was charged with 400g of didecylmethylamine, 72 g of methyl chloride, and 112 g of diethyleneglycol. The reaction solution was heated to 95°–100° C. and held in reaction at that temperature for five hours. A charge of 112 g of water was added to the reaction solution and heating was continued for an additional hour. After the six hours of total reaction time, the reaction mass was cooled to ambient temperature. The flash point of the quaternary ammonium compound reaction solution was greater than 200° F.

EXAMPLE 6

A 3 liter flask was charged with 400 g of alkyldimethylamine (40% $C_{12}$, 50% $C_{14}$, 10% $C_{16}$), 327 g of benzyl chloride, and 556 g of propylene glycol. The reaction solution was heated to 95°–100° C. and held in reaction at that temperature for five hours. A charge of 299 g of water was added to the reaction solution and heating was continued for an additional hour. After the six hours of total reaction time, the reaction mass was cooled to ambient temperature. The flash point of the quaternary ammonium compound reaction solution was greater than 200° F.

EXAMPLE 7

A 2 liter autoclave was charged with 400 g of didecylmethylamine, 122 g of methyl bromide, and 112 g of propylene glycol. The reaction solution was heated to 95°–100° C. and held in reaction at that temperature for four hours. After the five hours of total reaction time, the reaction mass was cooled to ambient temperature. The flash point of the quaternary ammonium compound reaction solution was greater than 200° F.

Example 8

A 2 liter autoclave was charged with 400 g of didecylmethylamine (40% $C_{12}$, 50% $C_{14}$, 10% $C_{16}$), 122 g of methyl bromide, and 112 g of diethyleneglycol. The reaction solution was heated to 95°–100° C. and held in reaction at that temperature for four hours. After the five hours of total reaction time, the reaction mass was cooled to ambient temperature. The flash point of the quaternary ammonium compound reaction solution was greater than 200° F.

EXAMPLE 9

A 2 liter flask was charged with 400g of didecylmethylamine, 122 g of methyl bromide, and 112 g of PEG-300. The reaction solution was heated to 95°–100° C. and held in reaction at that temperature for four hours. After the five hours of total reaction time, the reaction mass was cooled to ambient temperature and analyzed. The flash point of the quaternary ammonium compound reaction solution was greater than 200° F.

EXAMPLE 10

A 3 liter flask was charged with 603 g of alkyldimethylamine (40% $C_{12}$, 50% $C_{14}$, 10% $C_{16}$), 442 g of benzyl bromide, and 494 g of propylene glycol. The reaction solution was heated to 95°–100° C. and held in reaction at that temperature for five hours. A charge of 475 g of water was added to the reaction solution and heating was continued for an additional hour. After the six hours of total reaction time, the reaction mass was cooled to ambient temperature. The flash point of the quaternary ammonium compound reaction solution was greater than 200 ° F.

EXAMPLE 11

A 3 liter flask was charged with 603 g of alkyldimethylamine (40% $C_{12}$, 50% $C_{14}$, 10% $C_6$), 435 g of benzyl bromide, and 519 g of propylene glycol. The reaction solution was heated to 95°–100° C. and held in reaction at that temperature for five hours. A charge of 519 g of water was added to the reaction solution and heating was continued for an additional hour. After the six hours of total reaction time, the reaction mass was cooled to ambient temperature. The flash point of the quaternary ammonium compound reaction solution was greater than 200° F.

EXAMPLE 12

A 3 liter flask was charged with 603 g of alkyldimethylamine (40% $C_{12}$, 50% $C_{14}$, 10% $C_{16}$), 437 g of benzyl bromide, and 779 g of propylene glycol. The reaction solution was heated to 95°–100° C. and held in reaction at that temperature for five hours. A charge of 260 g of water was added to the reaction solution and heating was continued for an additional hour. After the six hours of total reaction time, the reaction mass was cooled to ambient temperature. The flash point of the quaternary ammonium compound reaction solution was greater than 200° F.

In all embodiments of the method of the invention the reaction step is performed at temperatures from about 50° to 120° C. frown about 2 to 24 hours.

The improved quaternary ammonium compound solution of the invention has a flash point greater than 200° F. which will not crystallize upon storage at ambient temperatures and has a relatively long shelf life.

While a specific embodiment of the invention has been shown and described herein for purposes of illustration, the protection afforded by any patent which may issue upon this application is not strictly limited by the disclosed embodiment; but rather extends to all structures and arrangements which fall fairly within the scope of the claims which are appended thereto:

What is claimed is:

1. A method of making a non-crystallizing quaternary ammonium compound solution having a flashpoint of at least 200° C. and a concentration of up to about 80% by weight quarternary ammonium compound, said method comprising the steps of dissolving a dialkylmethylamine reactant and an alkyl halide reactant in an alkylene glycol or a dialkylene glycol having the formula

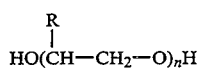

where R' is either H or $CH_3$ and n is 1 or 2, and heating said reactant solution to elevated temperatures until reaction completion.

2. The method of claim 1 wherein the alkyl halide is a benzyl halide, said method further comprises the step of adding water to the reaction solution after reaction completion and heating the aqueous reaction mixture.

3. The method of claim 1 wherein the dialkylmethylamine is selected from the group consisting of ($C_8$–$C_{24}$ alkyl) dimethylamine and di ($C_8$–$C_{24}$ alkyl) methylamine and the alkyl halide is selected from the group consisting of benzyl halides and methyl halides.

4. The method of claim 1 wherein said quaternary ammonium compound solution comprises about 50% to about 80% quaternary ammonium compound, with the remainder being glycol.

5. The method of claim 2 wherein the quaternary ammonium compound is a benzalkonium halide of the formula:

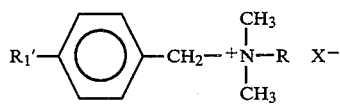

where R=$C_8$–$C_{24}$ alkyl, $R_1'$=$CH_3$, $C_2H_5$ or H and X=Cl or Br and said quaternary ammonium compound solution is about 50% quaternary ammonium compound, about 24% to about 42% alkylene glycol with the remainder being water.

6. The method of claim 5 wherein said alkylene glycol is propylene glycol.

7. The method of claim 5 wherein said quaternary ammonium compound is benzalkonium chloride.

8. The method of claim 1 wherein said quaternary ammonium compound is a dialkyldimethylammonium halide of the formula:

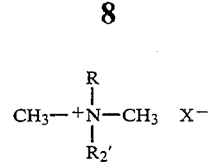

where R and $R_2'$=$C_8$–$C_{24}$ alkyl, and X=$Cl^-$ or $Br^-$ further comprising the step of adding water to the reaction solution to form a quaternary ammonium compound solution containing about 50% to about 80% quaternary ammonium compound, about 5.0% to about 50% alkylene glycol with the remainder being water.

9. The method of claim 8 wherein said alkylene glycol is propylene glycol.

10. The method of claim 8 wherein said quaternary ammonium compound is didecyldimethylammonium chloride.

11. The method of claim 2 wherein the quaternary ammonium compound is a mixture of a benzalkonium halide of the formula:

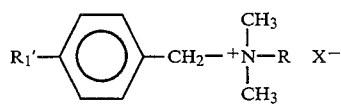

where
R=$C_8$–$C_{24}$ alkyl
$R_1'$=$CH_3$, $C_2H_5$, or H
X=$Cl^-$ or $Br^-$
and a dialkyldimethyl halide of the formula:

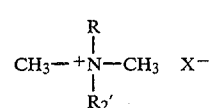

where
R=$C_8$–$C_{24}$ alkyl
$R_2'$=$C_8$–$C_{24}$ alkyl
X=Cl or Br
and said quaternary ammonium compound solution is about 50% quaternary ammonium compound, about 12.5% to about 50% alkylene glycol with the remainder water.

12. The method of claim 11 wherein said alkylene glycol is propylene glycol.

13. The method of claim 11 wherein said quaternary ammonium compound is a mixture of didecyldimethylammonium chloride and benzalkonium chloride.

14. The method of claim 2 wherein the quaternary ammonium compound is about 80% of the quaternary ammonium compound solution and said glycol is about 5.0% to about 20% of said solution with the remainder being water.

15. The method of claim 14 wherein said quaternary ammonium compound is a benzalkonium halide of the formula:

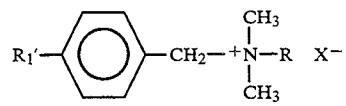

where R=$C_8$–$C_{24}$ alkyl, $R_1'$=$CH_3$, $C_2H_5$ or H and X=$Cl^-$ or $Br^-$ and said quaternary ammonium compound solution is about 80% quaternary ammonium compound, about 9.6% to about 16.8% alkylene glycol with the remainder being water.

16. The method of claim 15 wherein said alkylene glycol is propylene glycol.

17. The method of claim 15 wherein said quaternary ammonium compound is benzalkonium chloride.

18. The method of claim 1 wherein said quaternary ammonium compound is a dialkyldimethylammonium halide of the formula:

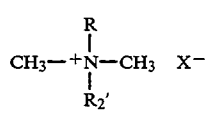

where R and $R_2' = C_8-C_{24}$ alkyl, and $X = Cl^-$ or $Br^-$ further comprising the step of adding water to the reaction solution to form a quaternary ammonium compound solution containing about 80% quaternary ammonium compound, about 5.0% to about 20% alkylene glycol with the remainder being water.

19. The method of claim 18 wherein said alkylene glycol is propylene glycol.

20. The method of claim 18 wherein said quaternary ammonium compound is didecyldimethylammonium chloride.

21. The method of claim 14 wherein the quaternary ammonium compound is a mixture of a benzalkonium halide of the formula:

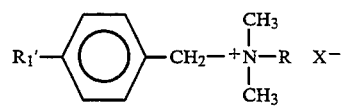

where
$R = C_8-C_{24}$ alkyl
$R_1' = CH_3$, $C_2H_5$, or H
$X = Cl^-$ or $Br^-$
and a dialkyldimethylammonium halide of the formula:

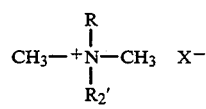

where
$R = C_8-C_{24}$ alkyl
$R_2' = C_8-C_{24}$ alkyl
$X = Cl^-$ or $Br^-$
and said quaternary ammonium compound solution is about 80% quaternary ammonium compound, about 5.0% to about 20% alkylene glycol with the remainder being water.

22. The method of claim 14 wherein said alkylene glycol is propylene glycol.

23. The method of claim 14 wherein said quaternary ammonium compound is a mixture of didecyldimethylammonium chloride and benzalkonium chloride.

* * * * *